(12) United States Patent
Dunki-Jacobs et al.

(10) Patent No.: US 11,925,352 B2
(45) Date of Patent: *Mar. 12, 2024

(54) SYSTEMS AND METHODS FOR INSTALLING A SURGICAL BUTTRESS ON AN END EFFECTOR AND USING SAME

(71) Applicant: Standard Bariatrics, Inc., Cincinnati, OH (US)

(72) Inventors: Adam R. Dunki-Jacobs, Cincinnati, OH (US); Jonathan R. Thompson, Cincinnati, OH (US); Caleb J. Hayward, Goshen, OH (US)

(73) Assignee: Standard Bariatrics, Inc., Cincinnati, OH (US)

( * ) Notice: Subject to any disclaimer, the term of this patent is extended or adjusted under 35 U.S.C. 154(b) by 0 days.

This patent is subject to a terminal disclaimer.

(21) Appl. No.: 17/961,618

(22) Filed: Oct. 7, 2022

(65) Prior Publication Data

US 2023/0035030 A1 Feb. 2, 2023

Related U.S. Application Data

(63) Continuation of application No. 17/733,790, filed on Apr. 29, 2022, now Pat. No. 11,490,892.

(60) Provisional application No. 63/181,711, filed on Apr. 29, 2021.

(51) Int. Cl.
*A61B 17/072* (2006.01)
*A61B 17/00* (2006.01)

(52) U.S. Cl.
CPC ............ *A61B 17/07207* (2013.01); *A61B 2017/00951* (2013.01); *A61B 2017/07257* (2013.01)

(58) Field of Classification Search
CPC ........ A61B 17/072; A61B 2017/00951; A61B 2017/07257
See application file for complete search history.

(56) References Cited

U.S. PATENT DOCUMENTS

| | | |
|---|---|---|
| 2006/0173470 A1 | 8/2006 | Oray et al. |
| 2007/0034669 A1* | 2/2007 | de la Torre ...... A61B 17/07207 227/180.1 |
| 2009/0095791 A1* | 4/2009 | Eskaros ............... A61B 17/072 227/175.1 |
| 2009/0206125 A1 | 8/2009 | Huitema et al. |
| 2012/0289979 A1* | 11/2012 | Eskaros ........... A61B 17/07292 606/151 |

(Continued)

OTHER PUBLICATIONS

Int'l. Search Report and Written Opinion issued in PCT/US22/27107; dated Sep. 23, 2022; 20 pages.

*Primary Examiner* — Nathaniel C Chukwurah

(57) ABSTRACT

A buttress device includes an applicator assembly including an applicator body, the applicator body being flexible, and a release liner. The release liner is coupled to the applicator body. The buttress device includes a buttress positioned on the applicator body, and a buttress fastener, the buttress fastener configured to couple the buttress to an end effector. The buttress fastener is configured to be releasably fastened to the release liner. The buttress device has a first configuration in which the buttress is coupled to the applicator assembly, and a second configuration in which the buttress is uncoupled from the applicator assembly, wherein the sacrificial tab is removed from the applicator assembly in the second configuration.

28 Claims, 8 Drawing Sheets

(56) References Cited

U.S. PATENT DOCUMENTS

| | | |
|---|---|---|
| 2018/0235617 A1 | 8/2018 | Shelton, IV et al. |
| 2019/0046186 A1 | 2/2019 | Dunki-Jacobs et al. |

* cited by examiner

SYSTEMS AND METHODS FOR INSTALLING A SURGICAL BUTTRESS ON AN END EFFECTOR AND USING SAME

REFERENCE TO RELATED APPLICATIONS

This application is a continuation of U.S. patent application Ser. No. 17/733,790, filed on Apr. 29, 2022, which was granted U.S. Pat. No. 11,490,892 on Oct. 19, 2022, which claims the priority benefit of U.S. Provisional Patent Application No. 63/181,711, filed on Apr. 29, 2021, each of which are incorporated herein by reference in their entirety.

TECHNICAL FIELD

Embodiments of the technology relate, in general, to surgical buttress technology, and in particular to systems and methods for installing a surgical buttress on an end effector and using same in a surgical procedure.

SUMMARY

In an embodiment, a buttress device includes an applicator assembly including an applicator body, the applicator body being flexible, and a release liner, the release liner comprising a sacrificial tab. The release liner is coupled to the applicator body. The buttress device also includes a buttress positioned on the applicator body and a buttress fastener, the buttress fastener being configured to couple the buttress to an end effector. The buttress fastener is configured to be releasably fastened to the release liner. The buttress device has a first configuration in which the buttress is coupled to the applicator assembly, and a second configuration in which the buttress is uncoupled from the applicator assembly, wherein the sacrificial tab is removed from the applicator assembly in the second configuration.

In an embodiment, a surgical stapling system includes a buttress device and a surgical stapler comprising an end effector having a first jaw and a second jaw. The buttress device may be inserted through the first jaw and the second jaw.

In an embodiment, a method of assembling a buttress device includes positioning the buttress on the applicator body and positioning the release liner on the buttress to adhere the buttress fastener to the buttress. The release liner becomes coupled to the applicator body.

In an embodiment, a method of applying a buttress to an end effector includes installing a buttress device on the end effector, removing the sacrificial tab from the applicator assembly to expose the buttress fastener, and manipulating the applicator body to adhere the buttress fastener to the end effector.

In an embodiment, a method of stapling an anatomical structure of a patient during a minimally invasive procedure includes providing an end effector comprising a first jaw having a first end, a second end, a longitudinal axis, and an anvil, the anvil comprising an anvil face, a second jaw having a first end, a second end, a longitudinal axis, and a cartridge retaining a plurality of staples, the cartridge having a cartridge face, wherein the first end of the first jaw is coupled to the first end of the second jaw; and a buttress, the buttress comprising a detachable portion and a remnant portion removably coupled by perforation ties, the remnant portion being coupled to the first jaw or the second jaw for a duration of the minimally invasive procedure. The method may also include inserting the end effector through a trocar to access the anatomical structure, positioning the cartridge face on the first side of the anatomical structure, positioning the anvil face on the second side of the anatomical structure, clamping the end effector on the anatomical structure, operating the end effector to urge the plurality of staples from the cartridge to staple the anatomical structure, and opening the end effector causing the perforation ties to rip.

BRIEF DESCRIPTION OF THE DRAWINGS

The present disclosure will be more readily understood from a detailed description of some sample embodiments taken in conjunction with the following figures.

DETAILED DESCRIPTION

Various non-limiting embodiments of the present disclosure will now be described to provide an overall understanding of the principles of the structure, function, and use of the apparatuses, systems, methods, and processes disclosed herein. One or more examples of these non-limiting embodiments are illustrated in the accompanying drawings. Those of ordinary skill in the art will understand that systems and methods specifically described herein and illustrated in the accompanying drawings are non-limiting embodiments. The features illustrated or described in connection with one non-limiting embodiment may be combined with the features of other non-limiting embodiments. Such modifications and variations are intended to be included within the scope of the present disclosure. Reference throughout the specification to "various embodiments," "some embodiments," "one embodiment," "some example embodiments," "one example embodiment," or "an embodiment" means that a particular feature, structure, or characteristic described in connection with any embodiment is included in at least one embodiment. Thus, appearances of the phrases "in various embodiments," "in some embodiments," "in one embodiment," "some example embodiments," "one example embodiment," or "in an embodiment" in places throughout the specification are not necessarily all referring to the same embodiment. Furthermore, the particular features, structures or characteristics may be combined in any suitable manner in one or more embodiments.

During stapling, it may be advantageous to provide a support buttress material through which the staples can be deployed. The buttress or support material may help distribute the pressure of multiple rows of staples, to improve the purchase of staples in tissue, or to maintain the integrity of a staple line. For example, a bioabsorbable or biological material can be provided on the faces of the anvil and/or cartridge through which the staples can be deployed during use. This buttress material, retaining the staples, can then be cut by a blade or knife and can be left within a patient.

Described herein are embodiments of a support buttress intended for stapling devices used during laparoscopic surgery that may be inserted through a trocar. Laparoscopic surgeries can include, for example, sleeve gastrectomy or resection of the stomach, but are not limited to these procedures.

Figure 1:
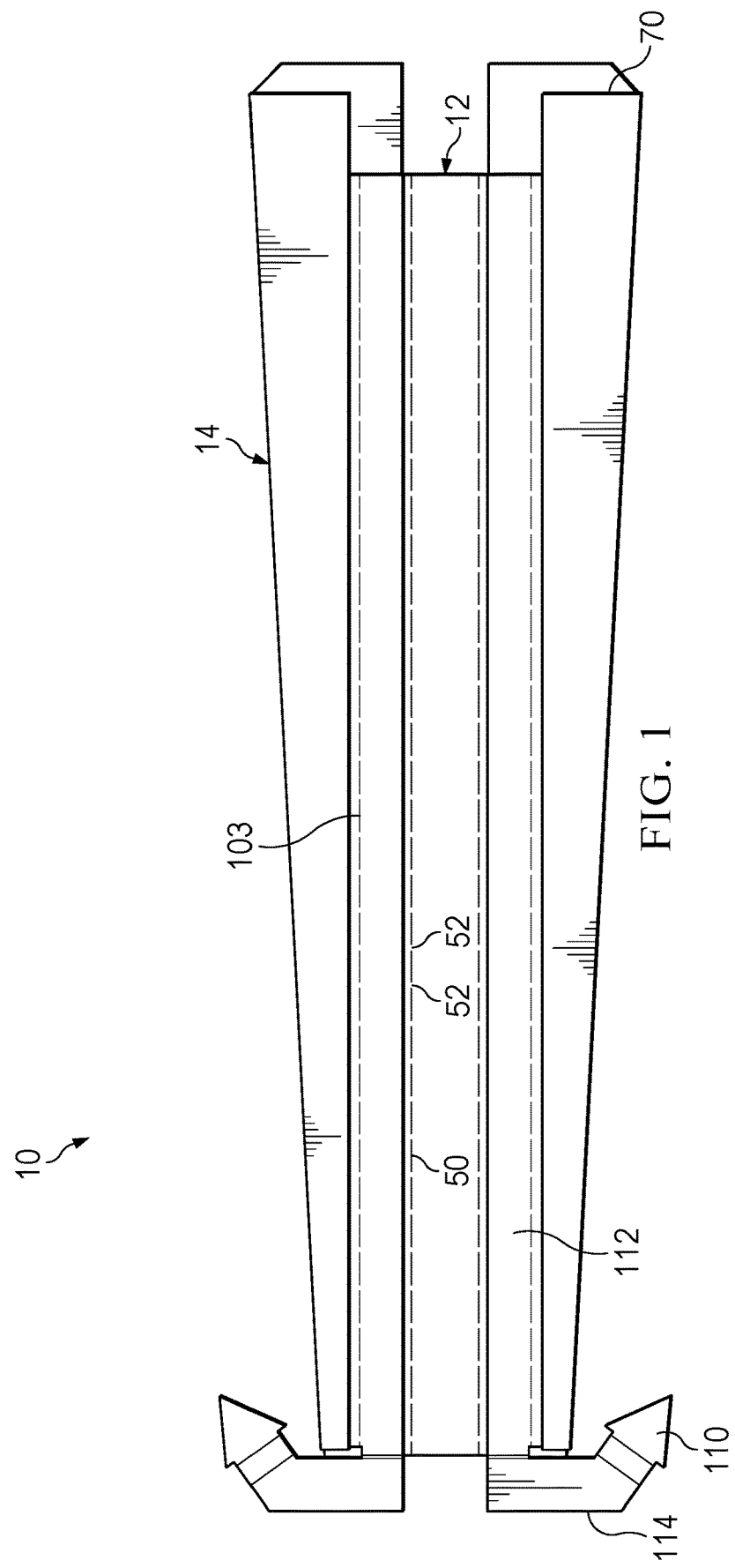
FIG. 1 is a top view of a buttress device according to an example embodiment.
Figure 2:
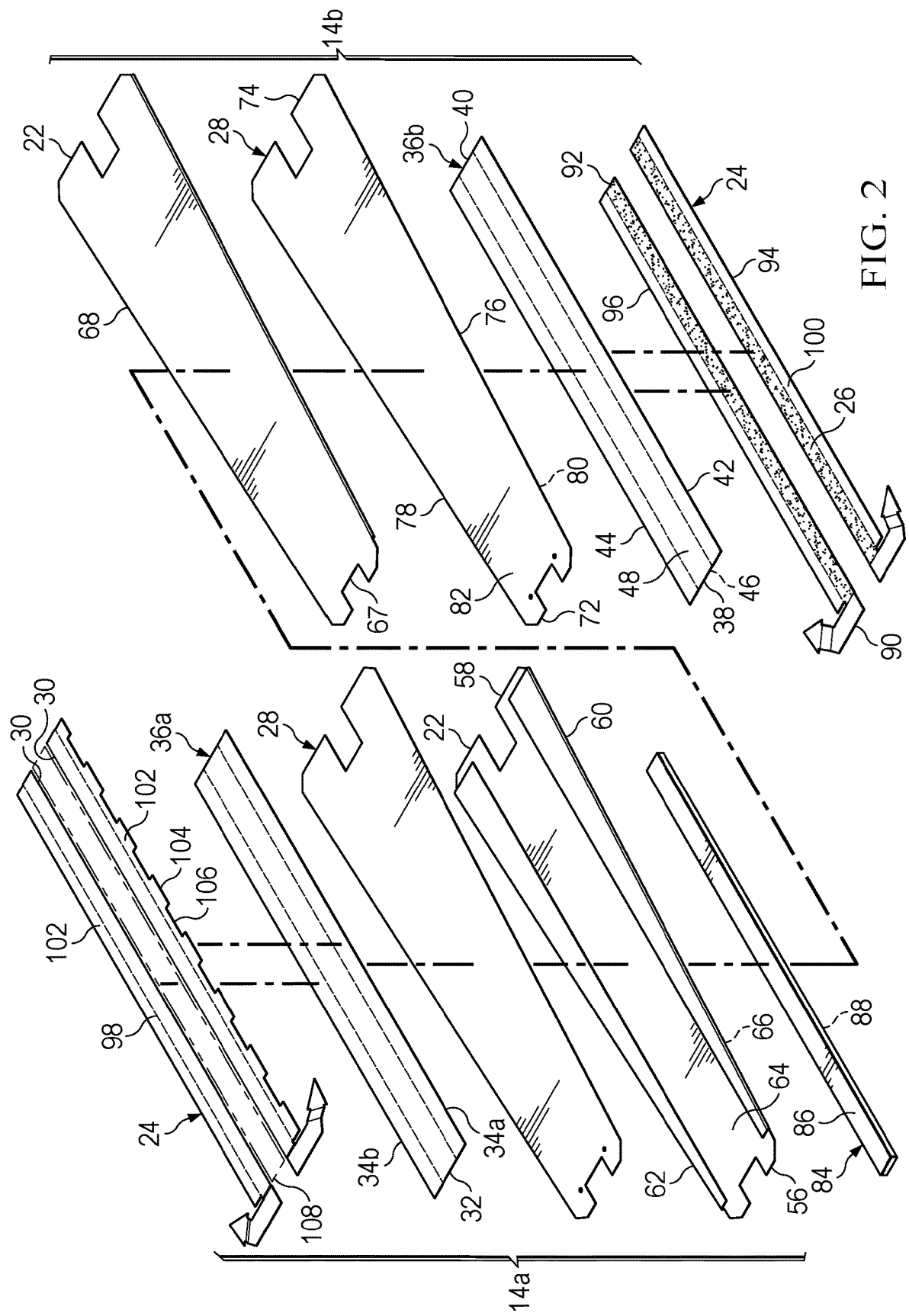
FIG. 2 is an exploded view of the buttress device of FIG. 1.

With reference to FIGS. 1 and 2, in an example embodiment, a buttress device 10 includes a buttress 12 removably coupled to an applicator assembly 14. The applicator assembly 14 is designed to carry the buttress 12 and align the buttress 12 on an end effector 16. The applicator assembly 14 may aid in the installation of the buttress 12 on first and second jaws 18, 20 of the end effector 16. The applicator assembly 14 may include an applicator body 22 and a release liner 24. The release liner 24 may include a buttress fastener 26 releasably fastened thereto. The release liner 24 is configured to removably couple the buttress 12 to the applicator body 22. The buttress 12 may be positioned on the applicator body 22 (or on an intermediate component, such as an applicator substrate 28). Then the release liner 24 may be positioned over the buttress 12 such that the buttress fastener 26 is fastened to the buttress 12. The adhesive on the applicator body secures the release liner 24 in place over a portion of the buttress 12.

The applicator assembly 14 is designed to be inserted into and aligned with jaws 18, 20 of the end effector 16. Once the applicator assembly 14 is aligned with the end effector 16, the end effector jaws 18, 20 may clamp down on the buttress 12. The release liner 24 may include sacrificial tabs 30 that, when removed, uncover the buttress fastener 26. In this configuration, the buttress 12 is uncoupled from the applicator assembly 14 and may be coupled to the end effector 16. The applicator assembly 14, or a separate tool, is then used to wrap or press the buttress 12 around the end effector 16 to attach it to the end effector 16. For example, the applicator body 22 may be manipulated to press the buttress fastener 26 against the end effector 16 to adhere the buttress 12 to the end effector 16. The buttress device 10 may be provided to the user with the buttress 12 coupled to the applicator assembly 14, allowing the end user to install the buttress 12 on the end effector 16 at the point of use. Alternatively, the buttress device 10 may be provided to the user pre-installed on the end effector 16. During a surgical procedure when the end effector 16 is clamped around tissue, a detachable portion 32 of the buttress 12 can be released from the end effector 16 while a remnant portion 34 remains on the end effector 16. To allow the user to release the detachable portion 32 of the buttress 12 from the end effector 16, the buttress device 10 includes a mechanism, such as a perforation tear, pull-string, or the like. The detachable portion 32 of the buttress 12 can be released from the end effector 16 before or after stapling the adjacent tissue.

Still referring to FIGS. 1 and 2, the buttress device 10 may include more than one subassembly. The buttress 12 may include one or more buttress members 36. For example, the buttress device 10 may include a first buttress member 36a for the first jaw 18 of the end effector 16 (e.g., anvil) and a second buttress member 36b for the second jaw 20 of the end effector 16 (e.g., cartridge). As used herein, terms such as "top" and "bottom" used to describe components of the buttress device 10 are relative to a respective jaw of the end effector. For example, "top" may refer to the side of the component facing the respective jaw. Thus, for a buttress to be applied to the anvil, the top surface of the buttress may face the anvil face while the bottom surface faces away from the anvil face. Where the buttress 12 includes multiple buttress members 36, the applicator assembly 14 may include an applicator subassembly 14a, 14b corresponding to each buttress member 36a, 36b.

As described above, the buttress 12 includes at least one buttress member 36. Each buttress member 36 may include a distal end 38, proximal end 40, first side 42, and second side 44 opposite the first side. The buttress member 36 may include a top surface 46 and a bottom surface 48. During the procedure, the buttress member 36 is stapled to the tissue. The buttress member 36 may include a portion intended to remain attached to the tissue after the procedure and a portion that is removed with the end effector. For example, the buttress member 36 may include the detachable portion 32 and one or more remnant portions 34. The remnant portion(s) 34 may be coupled to the end effector 16 for the duration of the procedure, while the detachable portion 32 remains attached to the tissue after the procedure is complete. The detachable portion 32 may be removably coupled to the remnant portion(s) 34. For example, the buttress member 36 may include a series of perforations 50 separated by perforation ties 52 that removably couple the detachable portion 32 and the remnant portion(s) 34. In an embodiment, the detachable portion 32 may be positioned between two remnant portions 34. For example, the buttress member 36 may include a first remnant portion 34a coupled to first side of the detachable portion 32 and a second remnant portion 34b coupled to a second side, which is opposite the first side, of the detachable portion 32. In such a configuration, the buttress member 36 may include two sets of perforations 50 coupling the detachable portion 32 to the first and second remnant portions 34a, 34b.

Figure 3:
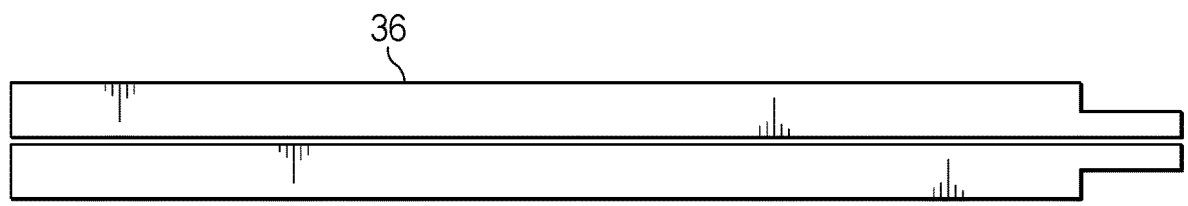
FIG. 3 is a top view of a buttress member according to an example embodiment having discrete sections along a length thereof.
Figure 4:
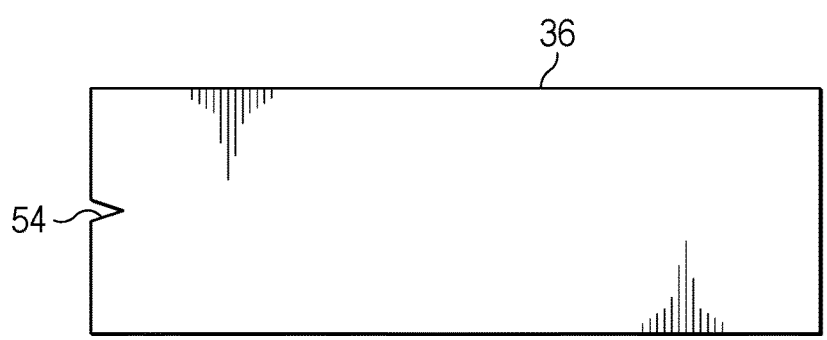
FIG. 4 is a top view of a buttress member according to an example embodiment having a distal slit.

The buttress member 36 may be made of any suitable buttress material, such as polymers (both permanent and bioabsorbable) as well as biological films. An example material for the buttress member includes a copolymer of polyglycolide (PGA) and trimethylene carbonate (TMC). Where a buttress device 10 includes more than one buttress member 36, the buttress members 36 can be identical or dissimilar. For example, a buttress device 10 may include differing "anvil" and "cartridge" buttress members 36. Having identical buttress members 36 would minimize the number of different components included in the buttress 12. The buttress members 36 may be symmetric or asymmetric (e.g., having a distinct "top" and "bottom" side). The buttress member 36 may include a proximal tab to allow the buttress member 36 to enter the proximal tissue stop of the end effector 16. Alternatively, or additionally, the buttress member may include a distal tab to enter the distal tissue stop of the end effector 16. The buttress member 36 may span the length and at least the width of the end effector anvil plates in a single continuous member to capture every staple fired from the end effector 16. In some embodiments, the buttress member 36 may include discrete adjacent sections that are grouped together via the applicator assembly, sectioned longitudinally (FIG. 3) or laterally. The adjacent sections may also be "bridged" together such that the entire width of the buttress member is not continuous. The buttress members 36 may be positioned to one side of the cut line, depending on the procedure, as reinforcing the staple line of excised tissue may not be necessary. In some embodiments, the buttress member 36 may include a slit 54 at the distal end thereof (FIG. 4) to initiate the cut line. The slit 54 may be positioned adjacent to the cut line. For example, the slit 54 may be in the center of the distal end of the buttress member 36. The slit 54 may be rectangular, triangular (bird's beak), or the like. In an example, the slit 54 may be segmented (e.g., to form a series of perforations) or may traverse the length of the buttress member 36 eliminating the need to cut the buttress member 36 during the surgical procedure.

The dimensions of the buttress 12 may vary based on the intended application. The width of the buttress members 36a, 36b may be the same or may differ. For example, the width of the anvil buttress member 36a is designed to wrap around the sides and/or top of the anvil providing enough contact to the end effector to properly adhere the buttress to the end effector. The distance that the buttress wraps around the sides of a jaw may vary. In an embodiment, the anvil buttress wraps fully around the anvil, maximizing the adhesion contact area. Wrapping the buttress around less than the entire jaw may improve the end effector's ability to slide through a trocar. The width of the cartridge buttress member 36b may be wider than the anvil buttress member 36a to compensate for the difference in width of the anvil and cartridge jaws. To minimize components and assembly complexity, identical buttresses may be used for both the anvil and cartridge. In various embodiments, the thickness may be in a range of, for example, about 0.1 to about 0.5 mm, about 0.2 to about 0.3 mm. The thickness may be about 0.26 mm. The average density may be in a range of, for example, about 0.1 to about 1.7 g/cm$^3$, or about 0.25 to about 1.34 g/cm$^3$. In various embodiments, the tensile stress of the buttress material may be in a range of about 700 to about 1300 psi, about 900 to about 1100 psi, or about 950 to about 1000 psi. The tensile stress may be, for example, about 983 psi.

The number and dimensions of the perforations 50 and perforation ties 52 may vary. The perforation ties 52 are configured to have a relatively high burst strength and a relatively low tear strength. The relatively high burst strength helps prevent the perforation ties 52 from unintentionally ripping while, for example, tissue is being positioned between the jaws 18, 20 of the end effector 16. The relatively low tear strength improves the ease with which the detachable portion 32 of the buttress member 36 separates from the remnant portions 34 when the jaws 18, 20 of the end effector 16 open. The distal end of the line of perforations 50 may begin with a lead-in perforation (e.g., the distal edge of the buttress member 36 may be discontinuous).

The width and spacing of the perforation ties 52 may vary. The perforation ties 52 are configured to resist side loads during tissue manipulating and/or activation of the end effector. The width of the perforation tie 52 may be, for example, in a range of about 0.005 to about 0.1 inch, about 0.01 to about 0.05 inch, or about 0.01 to about 0.03 inch, or may be about 0.02 inch. The width of the perforation 50 (e.g., the opening) may be, for example, in a range of about 0.01 to about 1 inch, about 0.1 to about 0.5 inch, or about 0.1 to about 0.3 inch, or may be about 0.24 inch. The ratio of the width of the perforation 50 to the width of the perforation tie 52 may be, for example, in a range of about 5 to about 20, or about 10 to about 15, or may be about 12. In an embodiment, the buttress member 36 may include perforation ties 52 having different widths. For example, the buttress member 36 may include alternative perforation ties 52 having a first width and a second width different than the first width.

The mechanical characteristics of the perforation ties 52, such as the burst strength and the tear strength, may vary. The burst strength (% hold) of the perforation ties 52 may be calculated based on the tooth per inch (number of perforation teeth that produce a "cut" in the perforation pattern per inch) times the tie width. In various embodiments, the burst strength (% hold) may be in a range of, for example, about 5 to 100%, about 5 to about 50%, about 5 to about 20%, about 5 to about 10%, or about 7 to 100%. The burst strength may be, for example, about 7.7%. In various embodiments, the tooth per inch (TPI) may be in a range of about 1 to about 10, about 1 to about 5, about 3 to about 4. The TPI may be, for example, about 3.4. The tear strength is a function of the tie width, material thickness, and the maximum tensile stress of the material. The tear strength may be equal to the cross-sectional area of the perforation tie 52 (thickness× width) times the tensile stress of the buttress material. In various embodiments, the perforation tear strength of a single perforation tie 52 may be in a range of greater than 0 to about 1 lbF, greater than 0 to about 0.5 lbF, about 0.1 to about 0.3 lbF. The perforation tear strength may be, for example, about 0.197 lbF. The tear strength can be varied based on changes in the perforation tie width, material thickness, and the maximum material tensile stress.

Referring again to FIGS. 1 and 2, the applicator assembly 14 is used to apply the buttress 12 to the end effector 16. In an embodiment, the applicator assembly 14 may include the applicator body 22 and the applicator substrate 28. Where the applicator assembly 14 includes subassemblies, each subassembly may include an applicator body 22 and an applicator substrate 28. The applicator assembly 14 may be disposable. In various embodiments, an applicator assembly 14 may include pull tabs. For example, where the buttress device includes more than one applicator subassemblies, one or both of the applicator subassemblies may include pull tabs to ease in separating the applicator bodies. The pull tabs may be, for example, rectangular or circular. The applicator bodies 22 may instead have recesses that allow for easier separation of the applicator bodies 22.

Each applicator body 22 may include a distal end 56, proximal end 58, first side 60, and second side 62 opposite the first side. The applicator body 22 may include a top surface 64 and a bottom surface 66. The applicator body 22 may include lateral and longitudinal alignment features, such as cutouts 67, to ensure proper alignment when the buttress device is installed on the end effector 16. The applicator body 22 may be made of, for example, any thickness of flexible cardstock, suture board, chipboard, like SBS (solid bleached sulfite), or any other semi-flexible member such as semi-compliant foam, rubber, silicone, or plastic. An example material for the applicator body 22 may be polyester. The applicator body 22 may include adhesive over a portion of or the entirety of the top surface 64. The adhesive may be, for example, an acrylic adhesive. The adhesive may be used to couple the release liner 24 to the applicator body 22. To further secure the release liner 24 in place, portions of the applicator body 22 may be folded over the edges of the release liner 24. For example, outer edges 68 of the applicator body 22 may fold over the top surface 64 of the applicator body 22 to result in folded portions 70. The folded portions 70 do not extend over the sacrificial tabs 30. In other words, the sacrificial tabs 30 remain uncovered. In the folded configuration, a portion of the bottom surface 66 of the applicator body 22 is visible from the top of the applicator body 22. In an embodiment, the bottom surface 66 of the applicator body 22 is configured to include printed indicia, such as symbols or instructions. The indicia may be visible on the folded portions 70.

Still referring to FIG. 2, each applicator substrate 28 may include a distal end 72, proximal end 74, first side 76, and second side 78 opposite the first side. The applicator substrate 28 may include a top surface 80 and a bottom surface 82. The applicator substrate 28 may be fabricated from any thin, flexible, hypoallergenic material and/or biocompatible material such as 4 mil LDPE. An example material for the applicator substrate 28 is polyester. The applicator substrate may provide additional strength to the applicator body 22. In an embodiment, the applicator substrate 28 spans the width and length of the buttress member 36. Where the applicator body 22 includes adhesive, the applicator substrate 28 may cover a portion of the adhesive to prevent the buttress 12 from becoming adhered to the applicator body 22. Adhesive on the sides of the top surface 64 of the applicator body 22 may remain uncovered by the applicator substrate 28. The buttress member 36 may be positioned over the applicator substrate 28. In an embodiment where the applicator assembly 14 does not include an applicator substrate 28, the portion of the applicator body 22 configured to be in contact with the buttress member 36 may be free from adhesive. In some embodiments, one or more of the applicator substrate or the adhesive is discontinuous.

Where the buttress device 10 includes more than one applicator subassembly, the applicator subassemblies may be fastened together. In some embodiments, the applicator subassemblies may be fastened together in the region where the jaws of the end effector will clamp together. The applicator subassemblies may be fastened together by glue, tape, staples, stitches, or the like.

With reference to FIG. 2, in various embodiments, the buttress device 10 may include a compliant member 84 positioned between the applicator subassemblies. When the jaws 18, 20 are clamped, the buttress members 36*a*, 36*b* and applicator subassemblies 14*a*, 14*b* compress the compliant member 84, which helps hold the buttress device 10 in place between the jaws 18, 20. The compliant member 84 is designed to provide thickness to the region adjacent to the end effector 16 and cause the jaws 18, 20 of the end effector 16 to provide compression to the buttress 12 during installation. The compliant member 84 may be adhered to the applicator body 22. Where the applicator assembly 14 includes multiple applicator subassemblies, the compliant member 84 may be adhered to each applicator body 22. The compliant member 84 may include adhesive on a top surface 86 and a bottom surface 88 and may initially include temporary liners to prevent unintentional adhesion. The user may remove the temporary liner to adhere the compliant member 84 to the respective applicator body 22. In various embodiments, the compliant member 84 may be continuous along the region adjacent to the end effector 16, sectioned longitudinally, or sectioned laterally. The compliant member 84 may extend along a length of the applicator body 22, extend along a proximal portion, or extend along a distal portion. In an embodiment, a thickness of the compliant member 84 may be tapered, for example, longitudinally.

The compliant member 84 may include a distal end, a proximal end, a first side, and a second side opposite the first side. The compliant member may be fabricated from foam, such as an adhesive-backed crosslink polyethylene foam (e.g., 2A Volara®), or any other hypoallergenic compliant member, such as folded (fluted) chipboard, rubber, or silicone. In an embodiment, the applicator bodies are each a die-cut bleached 0.009" cardstock member, and the compliant member is a strip of ³⁄₃₂" thick and ³⁄₈" wide foam. The compression may vary. For example, the foam compression at 25% deflection may be in a range of about 1 psi to about 10 psi, or may be about 5 psi.

Figure 5:
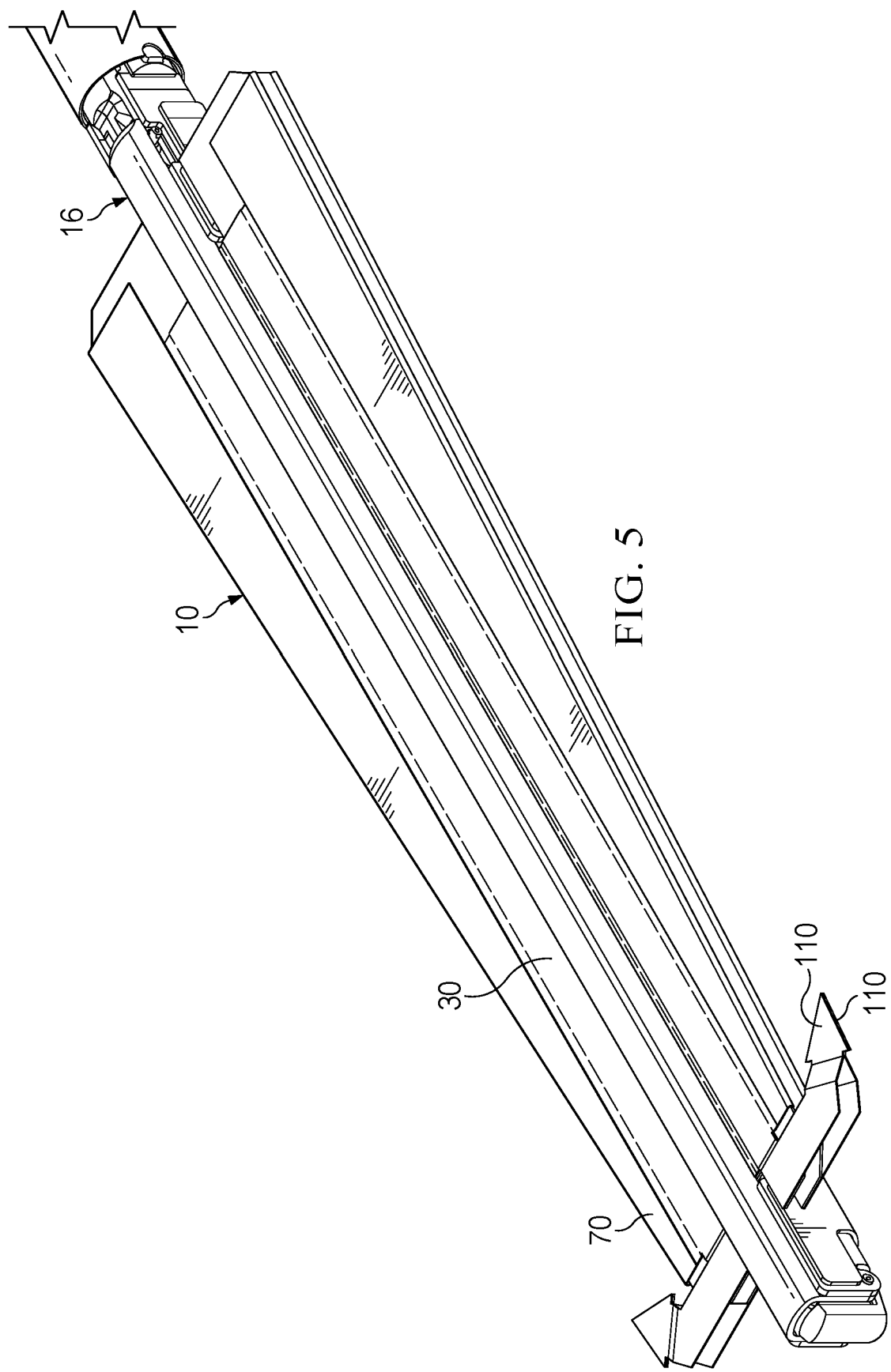
FIG. 5 is a perspective view of the buttress device of FIG. 1 with the buttress assembly being installed on an end effector.

With reference to FIGS. 1, 2, and 5, in various embodiments, the release liner 24 is configured to temporarily couple the buttress 12 to the applicator body 22. Each release liner 24 may include a distal end 90, proximal end 92, first side 94, and second side 96 opposite the first side. The release liner 24 may include a top surface 98 and a bottom surface 100. The release liner 24 may include side portions 102 configured to be coupled to the applicator body 22, as discussed above, and sacrificial tabs 30 removably fastened to the side portions 102 via perforations 103. The side portions 102 may include alternating projections 104 and recesses 106. For illustration purposes, projections 104 and recesses 106 are only illustrated on one side of the top release liner 24 in FIG. 2, though the technology is not so limited. When the edges of the applicator body 22 are folded over the side portions 102 of the release liner 24, the recesses 106 allow for areas where the applicator body 22 is adhered to itself while the applicator body 22 is adhered to the projections 104 of the release liner 24. The release liner 24 may further include a detachable center portion 108 removably fastened to the sacrificial tabs 30 (e.g., via perforations). After the buttress device 10 is assembled and before it is positioned on the end effector 16, the detachable center portion 108 may be removed to expose a portion of the buttress 12. The side portions 102, sacrificial tabs 30, and the detachable center portion 108 may be releasably coupled using features other than perforations (e.g., stitched together). The sacrificial tabs 30 may each include a grip 110. For example, sacrificial tab 30 may include a longitudinal portion 112 extending along the length of the buttress device 10 and an extension portion 114 extending laterally from the longitudinal portion 112. The extension portion 114 may fold over itself to provide additional strength. The grip 110 may be positioned at the end of the extension portion 114. The grips 110 of adjacent sacrificial tabs 30 may be coupled. For example, the grips 110 may be adhered together using, for example, an adhesive tab. The grip 110 may be shaped to provide an indication of the direction that the grip 110 should be pulled to remove the sacrificial tabs 30 from the buttress device 10. For example, the grips 110 may be shaped as an arrow. In an embodiment where the top surface 98 of the release liner 24 does not include a release coating, the adhesive tab may provide a better adhesion to the folded over grip 110 than the buttress fastener 26 provides to the bottom surface 100 of the release liner 24.

The release liner 24 may be made of, for example, Kraft paper or a plastic, such as polyester. The release liner 24 may include a release coating, such as a silicone release coating or a fluorosilicone release coating. The release coating may be on one or both sides of the release liner 24. The release coating may be continuous or discontinuous. During assembly of the buttress device 10, the buttress fastener 26 may be releasably adhered to the release liner 24. In an example, the buttress fastener 26 removably adheres the side of the release liner 24 including the release coating.

Still referring to FIG. 2, as described above, the buttress 12 may be attached to the end effector by the buttress fastener 26. The buttress fastener 26 ensures that the buttress 12 is taut and aligned relative to the lateral and longitudinal alignment features on the applicator assembly 14. In some embodiments, the buttress fastener 26 may be a medical-grade transfer adhesive. In other embodiments, the buttress fastener 26 may include high-tack, hypoallergenic, double-sided tape, such as Medical Tape 1567 from 3M™, single-sided tape, glue like cyanoacrylate, staples, or the like. An example medical-grade transfer adhesive is a synthetic rubber-based adhesive, such as 1504XL Hi Tack Medical Transfer Adhesive from 3M, or an acrylic adhesive. The buttress fastener 26 may include discrete segments. For example, the buttress fastener 26 may include two longitudinal strips of adhesive. As discussed above, the top of the buttress fastener 26 may be releasably adhered to the release liner 24, which is used to position the buttress fastener 26 on the buttress 12 during assembly of the buttress device 10. A temporary liner may be removed from the bottom of the buttress fastener 26 opposite the release liner 24 before positioning it on the buttress 12. The temporary liner may prevent the buttress fastener 26 from unintentionally adhering to something other than the buttress 12.

In various embodiments, the buttress fastener 26 may be continuous along the length of the buttress 12 to maximize adhesion, sectioned longitudinally, or sectioned laterally. The buttress fastener may instead not include an adhesive and may include a row of staples, rivets, tacks, or the like, to fasten the buttress to the applicator. The buttress fastener 26 is designed to fasten the buttress 12 to the end effector 16 but also to provide a fastening force to the end effector that is greater than the force to rip the perforations, as discussed herein. Additionally, the characteristics of the release liner 24 and the adhesion of the buttress fastener 26 are designed as to not delaminate the buttress fastener 26 from the buttress 12 when the release liner 24 is removed. Because the jaws 18, 20 of the end effector 16 may have a non-stick coating (e.g., PTFE), the buttress fastener 26 is configured to have a tack strong enough to hold the remnant portion 34 of the buttress to the end effector 16 while the perforation ties 52 are tearing. The adhesive 90° peel force to the jaws 18, 20 of the end effector 16 ("peel force") may be varied by changes in the surface area over which the buttress fastener 26 extends, using a higher surface energy substrate, etc. In various embodiments, the peel force may be in a range of about 0.1 to about 5 lbF, about 0.5 to about 5 lbF, about 0.5 to about 3 lbF, about 0.6 to about 5 lbF, or about 0.6 to about 2 lbF, or may be about 0.6 lbF. In an embodiment, the minimum 90° peel force of the buttress fastener 26 to the jaws 18, 20 of the end effector 16 is greater than the tear strength of the perforation ties 52.

To assemble the buttress device 10, the temporary liner(s) (FIG. 2) may be removed from the applicator body 22 to expose the adhesive. If an applicator substrate 28 is being used, it may be positioned over the applicator body 22. The buttress 12 may then be positioned on the applicator substrate 28 (or the applicator body 22). The temporary liner may be removed from the buttress fastener 26, and the release liner 24 may be positioned on the buttress member 36 with the buttress fastener 26 facing the top surface 46 of the buttress member 36. The outer edges 68 of the applicator body 22 may be folded over the side portions 102 of the release liner 24. If the release liner 24 extends entirely over the buttress 12, the detachable center portion 108 may be removed to expose a portion of the buttress 12. The sacrificial tabs 30 remain in place over the buttress fastener 26. The extension portion 114 of the sacrificial tabs 30 may be folded over and adjacent grips 110 may be adhered to each other. Multiple buttress and applicator subassemblies may be made in the same manner. If used, a compliant member 84 may be coupled to the applicator body or bodies 22. To do so, a temporary liner may be removed from the compliant member 84 to adhere it to the applicator body 22.

The components may include features used during assembly but removed before application. For example, the applicator body, applicator substrate, buttress, and release liner may include punctured tabs. The punctures on the punctured tabs may be positioned over an alignment feature, such as dowel rods, during assembly. This helps ensure that the components are properly positioned. After assembly, the punctured tabs may be removed.

Figure 6:
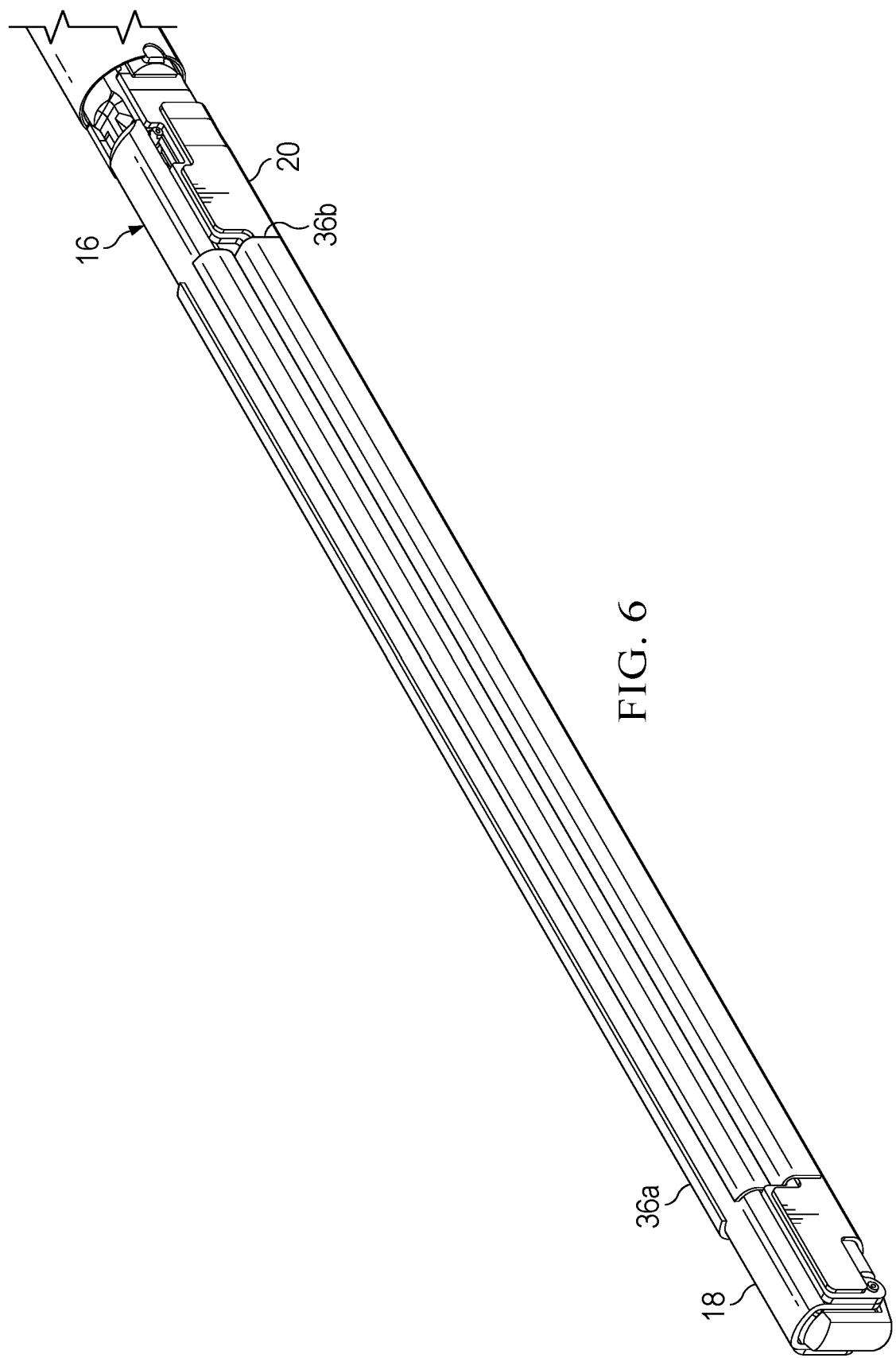
FIG. 6 is a perspective view of the buttress of the buttress device of FIG. 1 coupled to the end effector.

To apply the buttress 12 to the end effector 16, the buttress device 10 is inserted between the jaws 18, 20. When the buttress device 10 is positioned in the end effector 16, as shown in FIG. 5, the buttress 12 may be separated from the applicator assembly 14. To remove the sacrificial tabs 30, the user grabs the grips 110 of the sacrificial tabs 30 and pulls along the length of the buttress device 10 to rip the perforations and to expose the buttress fastener 26. At this point, the buttress 12 is positioned on but not coupled to the applicator assembly 14. The top of the buttress 12 may be entirely exposed. The buttress 12 may be fastened to the end effector 16 by bending the sides of the applicator assembly 14 around the jaws to adhere the buttress fastener 26 to the jaws 18, 20. FIG. 6 shows the buttress 12 adhered to the end effector 16.

The perforations 103 may traverse the length of the release liner 24 and cut through the ends of the release liner 24, providing a "starting" or lead-in perforation to ensure the reliability of the mechanism. The sacrificial tabs 30 may be designed to be pulled laterally and proximally, simultaneously, as seen by the directional arrow grips 110. This will help ensure that the perforations 103 rip and the release liner 24 is delaminated from the buttress fastener 26. Instead of the user pulling several grips 110 on each side of the buttress device 10, the upper and lower grips 110 may be fastened together to be separated with one pulling action. Other mechanisms may be used to release the buttress from the applicator assembly such as a chain stitch, a delaminating liner (found on consumer foam mounting tape, e.g., a Command™ strip), or the like.

Figure 7:
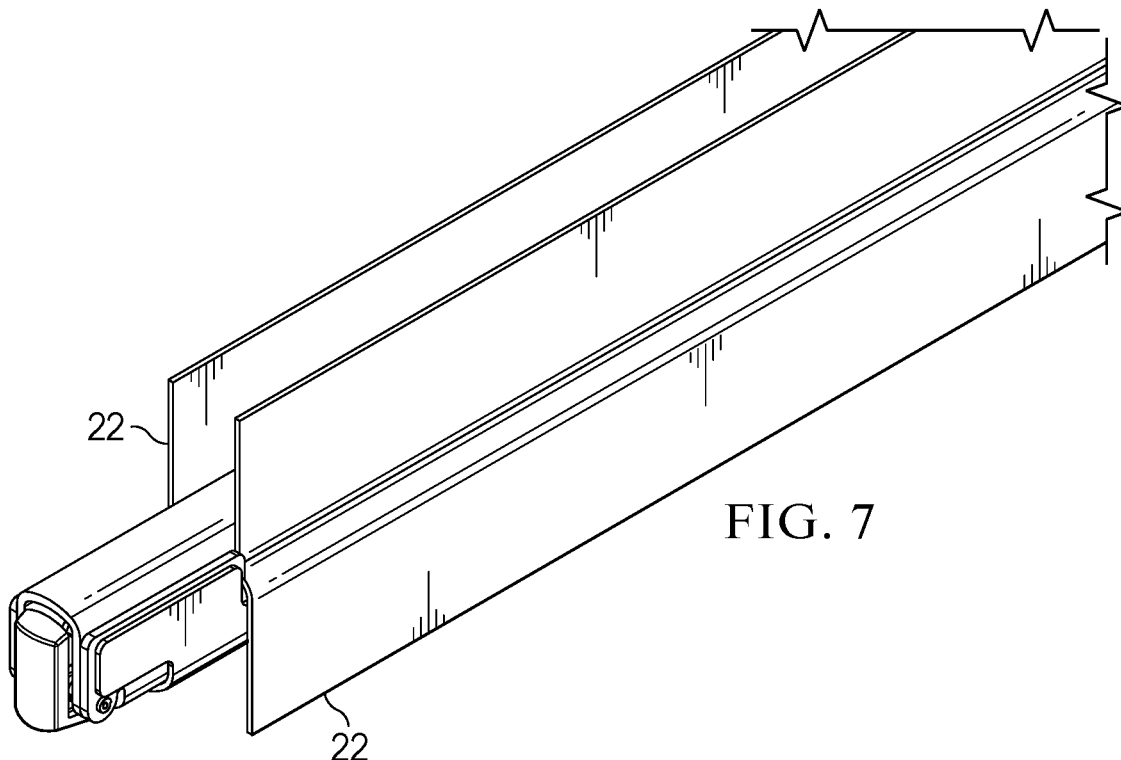
FIG. 7 is a perspective view of the buttress device of FIG. 1 showing manipulation of the applicator assembly to couple the buttress to the end effector.

After the sacrificial tabs 30 of the release liner 24 are separated from the buttress 12, the buttress 12 may be coupled to the end effector. The technique used to couple the buttress to the end effector may vary. As described above, the buttress fastener 26 may adhere the buttress to the end effector. For another example, the buttress may be coupled to a jaw via adhesion from tape, glue, or the like, or by mechanically fastening, such as tying, clipping, or the like. With reference to FIG. 7, the applicator assembly 14 may be used to couple the buttress 12 to the end effector 16. The sides of the applicator assembly 14 may be folded up and around the jaws 18, 20 to press the buttress fastener 26 against the jaws 18, 20.

Figure 8:
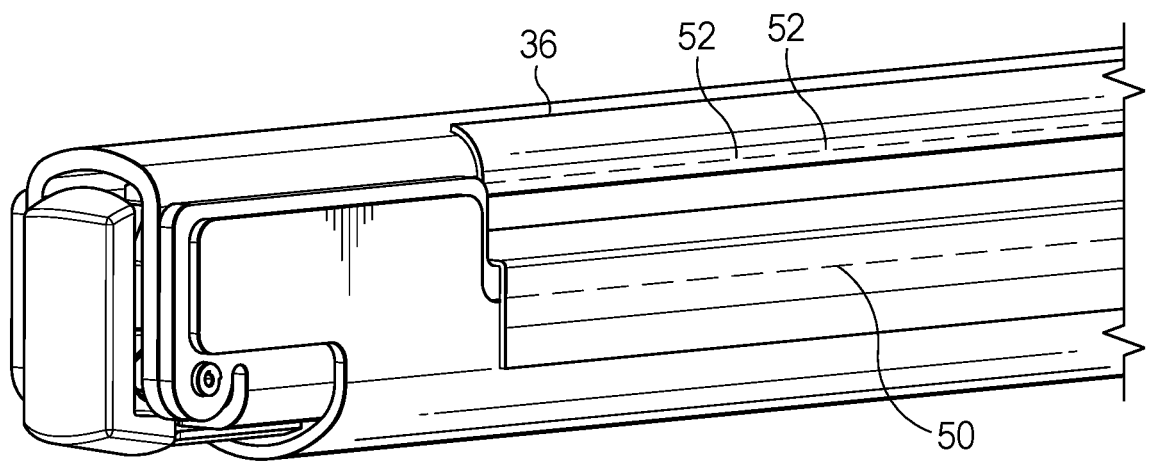
FIG. 8 is a perspective view of the buttress of the buttress device of FIG. 1 installed on an end effector showing perforations in the buttress member.

During the surgical procedure, the user may separate the detachable portion of the buttress member from the end effector so that the detached portion remains attached to the tissue. As described above, the buttress member may include perforations that rip to separate the detachable portion of the buttress member from the end effector. Perforations in the buttress member can be separated by various techniques. In an example shown in FIGS. 2 and 8, the buttress member 36 includes perforations 50 along a length thereof. In an embodiment, the perforations 50 may be positioned such that, when the buttress member 36 is coupled to a jaw 18, 20, the perforations 50 are positioned on a side of the jaw 18, 20. Opening the jaws 18, 20 of the end effector 16 causes the perforations 50 to rip. In some embodiments, the buttress device 10 may include a mechanism by which the user may selectively tear the perforations 50. An example includes a suture looped around the perforations 50. In use, an end of the suture extends out of the patient. The user may pull the suture from outside of the patient causing the suture to cut the perforations 50. In another example, two sets of perforations 50 are separated by a tab, and a suture is coupled to an end of the tab. Pulling the suture rips the tab away from the buttress member 36. A component other than a suture may be used to selectively tear the perforations 50. For example, an end of the tab may extend out of the patient during the procedure and can be pulled away from the buttress member 36.

Figure 9:
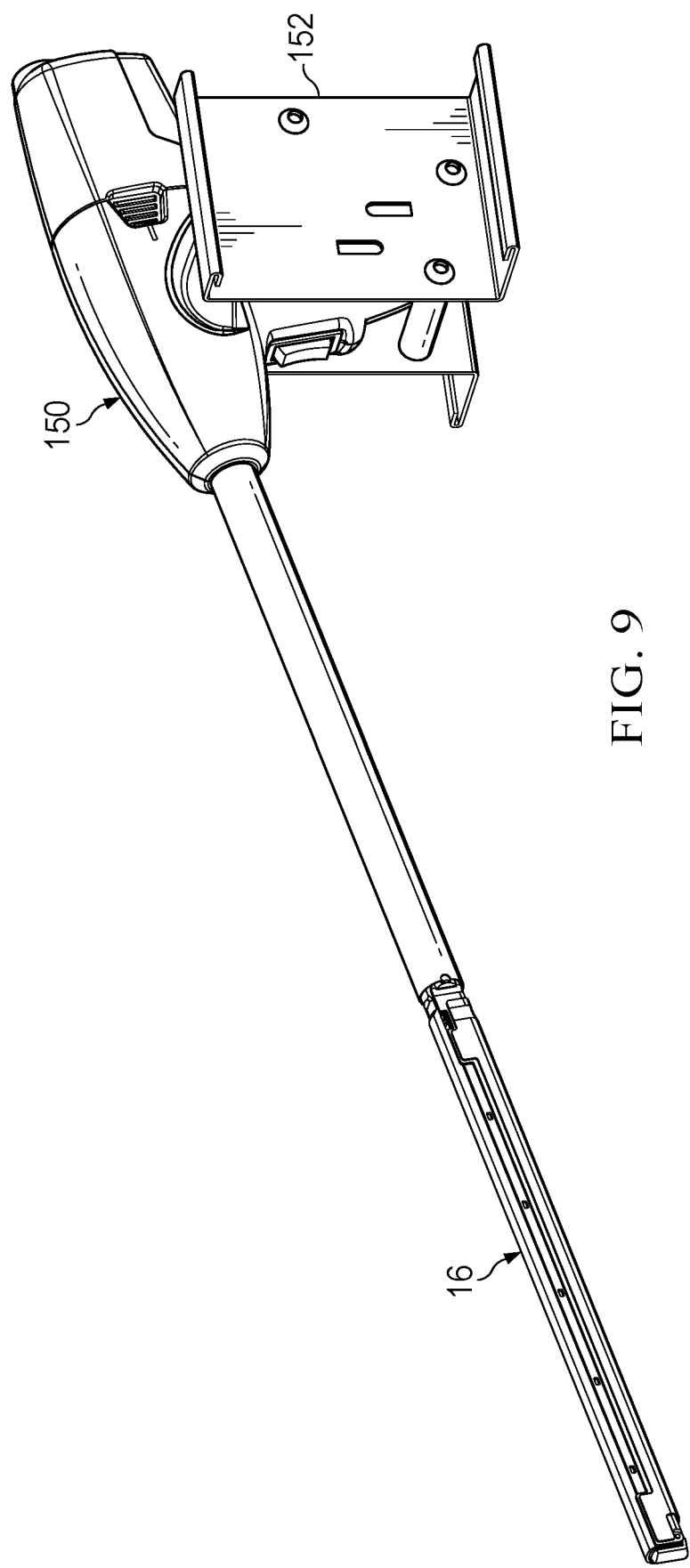
FIG. 9 is a perspective view of a stand according to an embodiment for holding an instrument during installation of a buttress assembly.
Figure 10:
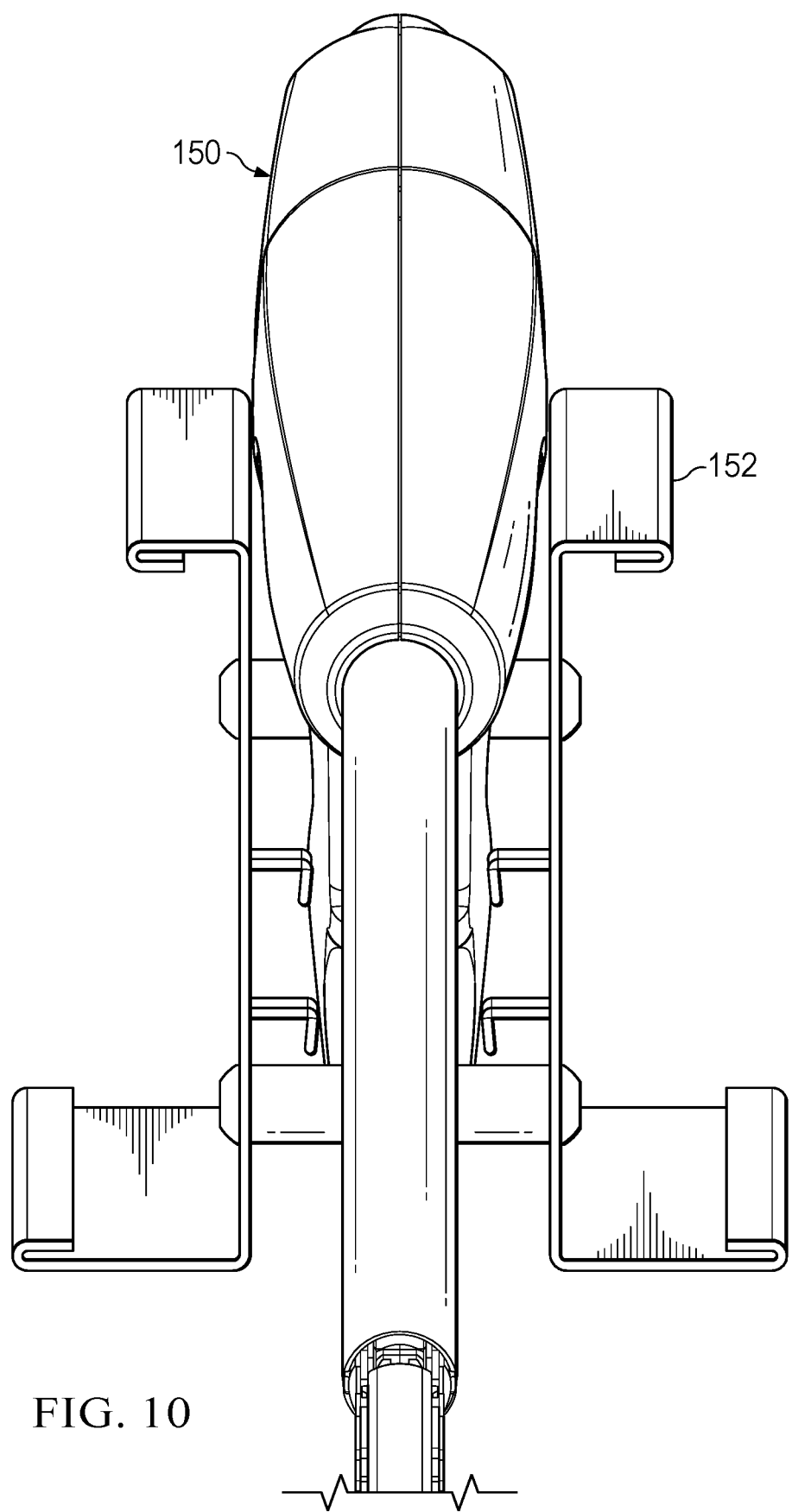
FIG. 10 is a front view of the stand of FIG. 9.

In an embodiment, a method of stapling an anatomical structure of a patient during a minimally invasive procedure, the anatomical structure having a first side and a second side, may include providing an end effector. The end effector may include a first jaw having a first end, a second end, a longitudinal axis, and an anvil, the anvil comprising an anvil face, a second jaw having a first end, a second end, a longitudinal axis, and a cartridge retaining a plurality of staples, the cartridge having a cartridge face. The first end of the first jaw may be coupled to the first end of the second jaw, and the second end of the first jaw may be coupled to the second end of the second jaw. The end effector may further comprise a buttress, the buttress comprising a detachable portion and a remnant portion removably coupled by perforation ties, the remnant portion being coupled to the first jaw or the second jaw for a duration of the minimally invasive procedure, and a knife coupled with and slidable relative to the first jaw or the second jaw. The method may include inserting the end effector through a trocar to access the anatomical structure, positioning the cartridge face on the first side of the anatomical structure, positioning the anvil face on the second side of the anatomical structure, clamping the end effector on the anatomical structure, operating the end effector to urge the plurality of staples from the cartridge to staple the anatomical structure, actuating the knife to cut the anatomical structure, and opening the end effector causing the perforation ties to rip. The end effector may then be removed from the trocar such that the detachable portion remains stapled to the anatomical structure and the remnant portion is still attached to the end effector.

Where the end user installs the buttress device on the end effector, an example embodiment includes a stand that aids the installation by keeping the end effector upright, steady, and allows it to be open and closed. FIGS. 9 and 10 show a stapling device 150 including the end effector 16 positioned on a stand 152. The stand may be reusable and made of material capable of withstanding repeated sterilization processes. For example, the stand may be made of metal, such as stainless steel, or of sterilizable or autoclavable plastic. The stand may be disposable, such as a thermoform stand, and may be incorporated in the device tray, already installed on the device. As show in FIG. 9, the tip of the end effector 16 may rest on the same plane (e.g., a table top) that the stand 152 rests on. In other embodiments, the stand may hold the end effector level or tilted, such as at 90 degrees. In an embodiment, the stand may include two separate parts: one part that constrains the handle of the device and one part that constrains the tip of the end effector. In an embodiment, the width of the applicator body may be determined based on the stand. For example, when a buttress device is inserted between the jaws while the stapling device 150 is positioned on the stand, the applicator body may be sized such that the applicator body does not contact the surface while the buttress is being pressed against the lower jaw.

In various embodiments, the applicator may include labeling, such as instructions. Installation errors may be mitigated with the use of instructions printed on the applicator reminding the user of the correct technique and order of operations to install the buttress on the end effector. The instructions may be incorporated on the applicator by printing, adhering stickers, or the like. The instructions may use warning fonts, colors, custom or universal action symbols, or any font, color, or symbol to communicate to the user. For example, labeling may be included on the folded-over surface of the top applicator body. In an embodiment, a sequential numbering scheme depicts the order of operations with large red text. Each step has black medium-sized text communicating to the user the technique of the current step. A custom symbol of the end effector orients the applicator in the yaw orientation. A custom symbol of the film pull tabs communicates to the user the features to pull. An example labeling on the top of the bottom applicator body, which is revealed once the top of the top applicator body is folded up. The sequential numbering and instruction step scheme continues. A universal "pinch" symbol instructs the user to pinch the applicator assembly. A universal "wrap" symbol accompanies the instruction step to instruct the user to wrap the applicator over the jaws of the end effector. A warning, in a warning color such as yellow, with extra-large text warns the user if the applicator assembly is upside down.

In an embodiment, the buttress may include a buttress and substrate film assembly. The buttress member may be removably fastened to the substrate film member. The mechanism to fasten the buttress member to the substrate film member may be any stitch capable of separating the members at will, a delaminating string or liner to separate adhesives (found on consumer foam mounting tape, e.g., a Command™ strip), a perforation mechanism where the perforation is cut into the film, like the proposed mechanism described above to separate the stapled buttress portion from the applicator, or where the perforation is cut into the buttress member. The mechanism may allow the user to separate the buttress member from the end effector at will, such as providing a tail to pull from outside of the patient, or by incorporating the mechanism into the end effector, which can separate the buttress member from end effector. The buttress member may be separated from the end effector manually or automatically via direct action from the user from outside of the patient or internally by a mechanism on the end effector. For example, the knife/firing mechanism (or other closure system) may be configured to automatically separate the buttress member from the end effector. In an embodiment, the applicator substrate of the applicator assembly may be configured to be attached to the end effector. In various embodiments, the substrate film member may be attached to the end effector via a separate fastening component like single-sided tape, double-sided tape, transfer adhesive, glue like cyanoacrylate, or the like.

In an embodiment where the buttress member has portions that are stitched together, the stitch may be unraveled to release the stapled portion of the buttress member from the end effector. The buttress fastener that couples the buttress to the end effector may also temporarily secure the suture tails. As discussed above, when the tail end of the stitch is secured, the stitch provides robust fastening. During assembly, transit, and installation, it may be desired that the stitch on the buttress is prevented from unraveling. During use, unraveling the stitch may provide an easy, reliable, and controlled release of the buttress member from the end effector from outside of the patient. To perform both functions, the tail ends of the stitch may be temporarily held in place by the buttress fastener (or a separate component). For example, the distal end and proximal end of the suture may be secured by a buttress fastener. Components other than the buttress fastener may be used to temporarily secure the end(s) of the suture. For example, a knot or bead may be included on the suture or thread that is pulled through the buttress or applicator substrate. Another method of terminating the threads is by adhering the double-sided tape member to the length of the threads. This method adheres the buttress assembly to the end effector, secures the ends of the threads by capturing them in the double-sided tape, and increases the force to pull the stitch. It will be recognized that other techniques that secure the integrity of the assembly and prevents accidental initiating of the release mechanism may be used. In an embodiment, to separate the buttress member from the applicator substrate, the tail ends of the stitch may be freed from the buttress fastener and pulled.

In an embodiment, an applicator assembly may be designed to fold from a flat configuration into a 3-dimensional configuration that aids in the installation of the buttress on the jaws of the end effector. For example, the sides of the applicator assembly are pinched to fold-up the applicator to form walls that adhere the buttress double-sided tape to the jaws of the end effector. The applicator body may be a static die cut member that aligns the buttress to the end effector while the buttress is adhered to the end effector jaws by a separate mechanism, such as a tool that slides down the end effector jaws, or by sacrificial "handles" on the applicator substrate that the user may manipulate and wrap the buttress around the end effector jaws. After fastening the buttress to the end effector, the handles may be torn off, via perforations, or the like, and discarded.

In various embodiments disclosed herein, a single component can be replaced by multiple components and multiple components can be replaced by a single component to perform a given function or functions. Except where such substitution would not be operative, such substitution is within the intended scope of the embodiments.

The foregoing description of embodiments and examples has been presented for purposes of illustration and description. It is not intended to be exhaustive or limiting to the forms described. Numerous modifications are possible in light of the above teachings. Some of those modifications have been discussed, and others will be understood by those skilled in the art. The embodiments were chosen and described in order to best illustrate principles of various embodiments as are suited to particular uses contemplated. The scope is, of course, not limited to the examples set forth herein, but can be employed in any number of applications and equivalent devices by those of ordinary skill in the art. Rather it is hereby intended the scope of the invention to be defined by the claims appended hereto.

What is claimed is:

1. A buttress device comprising:
an applicator assembly, the applicator assembly comprising:
an applicator body, the applicator body being flexible; and
a release liner,
wherein the release liner is coupled to the applicator body; and
a buttress positioned on the applicator body; and
a buttress fastener, the buttress fastener configured to couple the buttress to an end effector, wherein the buttress fastener is configured to be releasably fastened to the release liner;
wherein the buttress device has a first configuration in which the buttress is coupled to the applicator assembly, and a second configuration in which the buttress is uncoupled from the applicator assembly.

2. The buttress device of claim 1, wherein the buttress comprises a detachable portion and a remnant portion.

3. The buttress device of claim 2, wherein the detachable portion and the remant portion are copied by perforation ties, wherein a tear strength of the perforation ties is less than a peel force of the buttress fastener on the end effector.

4. The buttress device of claim 3, wherein the tear strength of a single perforation tie is in a range of greater than 0 to about 1 IbF.

5. The buttress device of claim 3, wherein the peel force is in a range of about 0.1 to about 5 IbF.

6. The buttress device of claim 2, wherein the buttress fastener is coupled to the remnant portion of the buttress.

7. The buttress device of claim 1, wherein the buttress fastener comprises adhesive.

8. The buttress device of claim 1, wherein the buttress comprises discrete sections separated longitudinally.

9. The buttress device of claim 1, wherein the applicator assembly further comprises an applicator substrate.

10. The buttress device of claim 9, wherein the applicator body has an adhesive top surface that couples the release liner to the applicator body.

11. The buttress device of claim 10, wherein edges of the applicator body are folded over sides of the release liner.

12. The buttress device of claim 11, wherein side portions of the release liner comprise alternating projections and recesses, wherein the edges of the applicator body are folded over the alternating projections and recesses.

13. The buttress device of claim 1, wherein a first surface of the release liner includes a release coating.

14. The buttress device of claim 1, wherein the release liner comprise a sacrificial tab.

15. The buttress device of claim 14, wherein the sacrificial tab comprises a longitudinal portion, an extension portion extending laterally from the longitudinal portion, the extension portion being folded over on itself, and a grip at an end of the extension portion.

16. The buttress device of claim 1, wherein the applicator assembly is a first applicator assembly, and the buttress device further comprises a second applicator assembly and a compliant member, the compliant member being coupled to the first applicator assembly and the second applicator assembly.

17. The buttress device of claim 1, wherein the buttress device has a third configuration in which the buttress is removed from the applicator assembly.

18. A surgical stapling system comprising:
the buttress device of claim 1; and
a surgical stapler comprising the end effector having a first jaw and a second jaw, wherein the buttress device is inserted through the end effector.

19. A method of assembling the buttress device of claim 1, the method comprising:
positioning the buttress on the applicator body; and
positioning the release liner on the buttress to adhere the buttress fastener to the buttress, wherein the release liner becomes coupled to the applicator body.

20. The method of claim 19, further comprising folding edges of the applicator body over side portions of the release liner.

21. The method of claim 19, wherein the applicator assembly is a first applicator assembly, and the buttress device further comprises a second applicator assembly and a compliant member, the method further comprising coupling the compliant member to the first applicator assembly and the second applicator assembly.

22. The method of claim 19, further comprising removing a temporary liner from the buttress fastener before positioning the release liner on the buttress.

23. The method of claim 19, further comprising removing a temporary liner from the applicator body to expose the adhesive top surface of the applicator body.

24. The method of claim 19, further comprising positioning an applicator substrate on the applicator body, and wherein positioning the buttress on the applicator body comprises positioning the buttress on the applicator substrate.

25. A method of applying a buttress to an end effector, the method comprising:
   installing a buttress device on the end effector, the buttress device comprising:
      an applicator assembly, the applicator assembly comprising:
         an applicator body, the applicator body being flexible; and
         a release liner,
            wherein the release liner is coupled to the applicator body;
      the buttress positioned on the applicator body; and
      a buttress fastener, wherein the buttress fastener is coupled to the buttress and releasably fastened to the release liner;
   exposing the buttress fastener; and
   manipulating the applicator body to adhere the buttress fastener to the end effector.

26. The method of claim 25, further comprising removing the applicator assembly from the end effector.

27. The method of claim 25, wherein the release liner comprises a sacrificial tab.

28. The method of claim 27, wherein the sacrificial tab comprises a longitudinal portion, an extension portion extending laterally from the longitudinal portion, the extension portion being folded over on itself, and a grip at an end of the extension portion.

* * * * *